US006403656B1

(12) United States Patent
Rivier et al.

(10) Patent No.: US 6,403,656 B1
(45) Date of Patent: Jun. 11, 2002

(54) USE OF PPAR-γ ACTIVATORS IN DERMATOLOGY

(75) Inventors: Michel Rivier; Irina Safonova, both of Nice; Serge Michel, Roquefort les Pins, all of (FR)

(73) Assignee: Galderma Research & Development S.N.C, Valbonne (FR)

( * ) Notice: Subject to any disclaimer, the term of this patent is extended or adjusted under 35 U.S.C. 154(b) by 0 days.

(21) Appl. No.: 09/582,614

(22) PCT Filed: Dec. 28, 1998

(86) PCT No.: PCT/FR98/02894

§ 371 (c)(1),
(2), (4) Date: Sep. 7, 2000

(87) PCT Pub. No.: WO99/34783

PCT Pub. Date: Jul. 15, 1999

(30) Foreign Application Priority Data

Dec. 31, 1997 (FR) ............................................. 97 16808

(51) Int. Cl.$^7$ .......................... A61P 17/02; A61P 17/08; A61K 31/193; A61K 31/195; A61K 31/426
(52) U.S. Cl. ...................... 514/861; 514/863; 514/864; 514/859; 514/887; 514/367; 514/369; 514/375; 514/377; 514/564; 514/567; 514/571
(58) Field of Search .......................... 424/401; 514/887, 514/861, 863, 864, 859, 367, 369, 475, 477, 564, 567, 569, 571

(56) References Cited

U.S. PATENT DOCUMENTS

| 5,443,844 A | | 8/1995 | McDaniel | |
| 5,594,015 A | * | 1/1997 | Kurtz et al. | 514/369 |
| 6,060,515 A | * | 5/2000 | Elias et al. | 514/256 |

FOREIGN PATENT DOCUMENTS

| EP | 0347056 | 5/1989 |
| WO | 9014824 | 12/1990 |
| WO | 9535108 | 12/1995 |
| WO | 9609055 | 3/1996 |
| WO | 9633724 | 10/1996 |
| WO | 9808089 | 2/1998 |
| WO | 9825598 | 6/1998 |
| WO | 9832444 | 7/1998 |
| WO | 9857631 | 12/1998 |

OTHER PUBLICATIONS

C.J. Kavanaugh et al: "Conjugated Linoleic Acid Modulation of PPAR–GAMMA in Mouse Keratinocytes", FASEB Journal, vol. 12, No. 4, Apr. 1998, p. A565 XP002078271.

S.A. Kliewer et al: Faty Acids and Eicosanoids Regulate Gene Expression Through Direct Interactions With Peroxisome Proliferator–Activated Receptors Alpha and Gamma, Proc. Natl. Acad. Sci., vol. 94, No. 9, Apr. 1997, pp. 4318–4323, XP002078272.

Lehmann J.M. et al, "An Antidiabetic Thiazolidinedione is a High Affinity Ligand for Peroxisome Proliferator–Activated Receptor Gamma (PPARGAMMA)", Journal of Biological Chemistry, vol. 270, No. 22, Jun. 2, 1995, pp. 12953–12956, XP000577082.

M.D. Bregman et al, "Inihibition of Human Melamona Growth By Prostaglandin A. D and J Analogues", Cancer Research, vol. 46, No. 6, 1986, pp. 2740–2744, XP002078273.

D.R. Buckle et al, "Non Thiazolidinedione Antihyperglycaemic Agents.1", Bioorganic & Medicinal Chemistry Letters, vol. 6, No. 17, 1996, pp. 2121–2126, XP002078274.

* cited by examiner

Primary Examiner—Edward J. Webman
Assistant Examiner—Helen Nguyen
(74) Attorney, Agent, or Firm—Burns, Doane, Swecker & Mathis, L.L.P.

(57) ABSTRACT

The invention concerns the use of at least one activator of receptors of the PPAR-γ type for preparing a pharmaceutical composition for treating skin disorders related to an anomaly of the differentiation of epidermic cells.

9 Claims, No Drawings

USE OF PPAR-γ ACTIVATORS IN DERMATOLOGY

The present invention relates to the use of at least one activator of receptors of PPAR-γ type for preparing a pharmaceutical composition, the composition being intended for treating skin disorders related to an abnormality of the differentiation of epidermal cells.

Many skin disorders exist which are related to an abnormality of the differentiation of epidermal cells; as examples mention may be made of psoriasis, eczema, dermatitides, common acne, keratoses, including ichthyosis, and skin cancers. This abnormality of the differentiation of epidermal cells is generally accompanied by a hyperproliferation of epidermal cells. To treat these disorders, various pharmaceutical approaches have been envisaged. However, no treatment at this time is entirely satisfactory. Thus there is a need to improve the existing treatments.

Peroxisomes are small organelles which are closely related to mitochondria and which contain a series of enzymes which are characteristic of the metabolism of hydrogen peroxide (catalase, urate oxidase, D-amino acid oxidase), and fatty acid β-oxidation enzymes. Peroxisome proliferators are principally groups of chemical products which comprise hypolipidaemiants such as clofibrate, herbicides and industrial plastics such as phthalate esters. These peroxisome proliferators are non-genotoxic carcinogens which activate receptors, which are termed PPARs, and which are part of the steroid nuclear receptor super-family. These receptors can be activated by peroxisome proliferators, they can also be activated by natural fatty acids, and they thus stimulate the expression of genes which encode enzymes involved in peroxisomal and mitochondrial β-oxidation, or alternatively which encode P450-4A6 fatty acid β-hydroxylase.

The set of references suggests a role for PPARs in the regulation of metabolism and the homeostasis of lipids.

PPAR receptors activate transcription by binding to DNA sequence elements, which are termed peroxisome proliferator response elements (PPRE), in the form of a heterodimer with retinoid X receptors (termed RXRs).

Three subtypes of human PPAR have been identified and described: PPARα, PPARγ and PPARδ (or NUC1).

In patent application WO 96/33724, it has been described that compounds which are selective for the PPARγs, such as a prostaglandin J2 or D2, are potential active agents for treating obesity and diabetes.

Moreover, in patent application WO 95/35108, it has been described that thiazolidinediones, more particularly ciglitazone, have an activity in the treatment of psoriasis by inhibiting the proliferation of keratinocytes.

The Applicant has just discovered that when the differentiation of human keratinocytes is induced with a high calcium concentration, the level of expression of the PPARs, more particularly of PPARγ, is increased. Also, the Applicant has observed that the level of expression of the PPARs, more particularly of PPARγ, in psoriatic lesioned skin is noticeably reduced with respect to that in non-lesioned skin.

Thus, a subject of the present invention is the use of at least one activator of receptors of PPAR-γ type for preparing a pharmaceutical composition, the composition being intended for treating skin disorders related to an abnormality of the differentiation of epidermal cells.

The pharmaceutical composition is preferably a dermatological composition.

"Activator of receptors of PPAR-γ type" is intended to mean, according to the invention, any compound which, in a transactivation test as described in Kliewer et al., Nature 358, 771–774, 1992, has an AC50 relative to PPAR-γ which is lower than or equal to 1 $\mu$M.

Preferably, the activator of receptors of PPAR-γ type has an AC50 relative to PPAR-γ which is lower than or equal to 200 nM, and advantageously which is lower than or equal to 50 nM.

Preferably, the activator of receptors of PPAR-γ type is specific, i.e. it has a ratio R1 of AC50 relative to PPAR-γ over AC50 relative to PPARα which is lower than or equal to $10^{-1}$. Preferably, R1 is lower than or equal to 0.05, and more advantageously is lower than or equal to 0.02.

The AC50 is the concentration of "activator" compound required to give 50% of an enzymatic activity (luciferase) which is a reporter of the activation due to the compound via one of the PPAR receptors, and more particularly of PPAR-α or PPAR-γ type.

The compounds more particularly used in the present invention are:
5-{4-[2-(methylpyrid-2-yl-amino)ethoxy]benzyl-thiazolidine-2,4-dione;
3-{4-[2-(benzoxazol-2-ylmethylamino)ethoxy]phenyl}-2-ethoxypropionic acid;
(+)-3-{4-[2-(benzoxazol-2-ylmethylamino)ethoxy]phenyl}-2-ethoxypropionic acid;
(−)-3-{4-[2-(benzoxazol-2-ylmethylamino)ethoxy]phenyl}-2-ethoxypropionic acid;
15-deoxy-$\Delta^{12,14}$-prostaglandin J$_2$(15-d PGJ2).

It is all the more surprising that the compounds used in the present invention treat this type of skin disorder, since some of them have a weak, or even no inhibitory activity on the proliferation of keratinocytes, such as 5-{4-[2-(methylpyrid-2-yl-amino)ethoxy]benzyl}thiazolidine-2,4-dione and 15-d PGJ2.

Preferably, the activator of receptors of PPAR-γ type used has a percentage of inhibition of keratinocyte proliferation which is less than or equal to 20% when it is used at a concentration which is lower than or equal to 100 nM (see example below).

The pharmaceutical composition according to the invention comprises a physiologically acceptable medium.

Other characteristics, aspects, subjects and advantages of the invention will emerge even more apparent upon reading the description which will follow, as well as the various concrete, but in no way limiting examples which are intended to illustrate it.

Among the disorders related to an abnormality of the differentiation of epidermal cells, more particularly keratinocytes, mention may be made more particularly of psoriasis, eczema, lichen planus, skin lesions associated with lupus, dermatitides such as atopic, seborrho or solar dermatitis, keratoses such as seborrhoeic keratosis, senile, actinic, light-induced or follicular keratosis, common acne, keloids, nevi, warts, ichthyoses and skin cancers.

Among the disorders related to an abnormality of the differentiation of epidermal cells, abnormalities of the barrier function, such as atopic dermatitis, eczema and psoriasis are preferably mentioned.

Administration of the composition according to the invention can be carried out via the enteral, parenteral or topical route. Preferably, the pharmaceutical composition is packaged in a form which is suitable for application via the topical route.

Via the enteral route, the composition, more particularly the pharmaceutical composition, can be in the form of tablets, gelatin capsules, dragees, syrups, suspensions, solutions, powders, granules, emulsions, microspheres or nanospheres or lipidic or polymeric vesicles which enable controlled release. Via the parenteral route, the composition can be in the form of solutions or suspensions for perfusion or for injection.

The compounds are used according to the invention are generally administered at a daily dose of about 0.001 mg/kg to 100 mg/kg of body weight, taken in 1 to 3 dosage intakes.

Via the topical route, the pharmaceutical composition according to the invention is more particularly intended for treatment of the skin and of the mucous membranes, and can be in the form of pasty ointments, creams, milks, creamy ointments, powders, impregnated pads, solutions, gels, sprays, lotions or suspensions. It can also be in the form of microspheres or nanospheres or lipidic or polymeric vesicles or polymeric patches and hydrogels which enable controlled release. This topical-route composition can be either in anhydrous form or in aqueous form.

The compounds are used via the topical route at a concentration generally between 0.001% and 10% by weight, preferably between 0.01 and 1% by weight, relative to the total weight of the composition.

The compositions as described above can of course also contain inert or even pharmacodynamically active additives or combinations of these additives, and in particular: wetting agents; depigmenting agents such as hydroquinone, azelaic acid, caffeic acid or kojic acid; emollients; hydrating agents such as glycerol, PEG-400, thiamorpholinone and derivatives thereof, or alternatively urea; anti-seborrhoeic agents or anti-acne agents such as S-carboxymethylcysteine and S-benzylcystamine and the salts or derivatives thereof, or benzoyl peroxide; antifungal agents such as ketoconazole or poly-4,5-methylene-3-isothiazolidones; antibacterial agents, carotenoids and in particular β-carotene; anti-psoriatic agents such as anthralin and derivatives thereof; eicosa-5, 8,11,14-tetraynoic acid and eicosa-5,8,11-triynoic acid, the esters and amides thereof and finally retinoids.

These compositions can also contain flavour-enhancing agents, preserving agents such as para-hydroxybenzoic acid esters, stabilizers, moisture regulators, pH regulators, osmotic pressure modifiers, emulsifying agents, UV-A and UV-B screening agents, and antioxidants such as α-tocopherol, butylhydroxyanisole or butylhydroxytoluene.

Of course, persons skilled in the art will take care to choose the optional compound(s) to be added to these composition in such a way that the advantageous properties which are intrinsically attached to the present invention are not, or are not substantially, altered by the addition envisaged.

Several examples will now be given, which are intended to illustrate the present invention, and which are in no way limiting.

EXAMPLE 1

AC50 and R1 of the PPARγ-activating Products as Described Above

The method used to determine the AC50s is that described in Kliewer et al., Nature 358, 771–774, 1992. Thus, the activating power of molecules, via PPARγ or PPARα, can be evaluated with a transactivation test in which HeLa cells were cotransfected with an expression vector encoding these receptors and a reporter plasmid containing a PPRE response element, which is cloned upstream of a portion of the SV40 virus promoter and of the luciferase gene. The cotransfected cells are treated for 24 hours with the molecules to be tested, and the luciferase activity is determined by luminescence.

Table 1 collates the results. For each molecule, the results are expressed in nM by the AC50 value, which thus represents the concentration of molecule to be tested which gives 50% of the maximum activity.

TABLE 1

|  | AC50 (nM) – PPARα | AC50 (nM) – PPARγ | R1 |
| --- | --- | --- | --- |
| Compound A | 2800 | 70 | 0.025 |
| Compound B | 2900 | 37 | 0.013 |
| Compound C | 4600 | 130 | 0.028 |
| Compound D | 1450 | 5 | 0.003 |
| Compound E | 2200 | 180 | 0.082 |

Compound A: 5-{4-[2-(methylpyrid-2-ylamino)-ethoxy]benzyl}thiazolidine-2,4-dione;
Compound B: 3-{4-[2-(benzoxazol-2-ylmethylamino)-ethoxy]phenyl}-2-ethoxypropionic acid;
Compound C: (+)-3-{4-[2-(benzoxazol-2-ylmethylamino)-ethoxy]phenyl}-2-ethyoxypropionic acid;
Compound D: (−)-3-{4-[2-(benzooxazol-2-ylmethylamino)-ethoxy]phenyl}-2-ethyoxypropionic acid;
Compound E: 15-deoxy-$\Delta^{12,14}$-prostaglandin $J_2$(15-d PGJ2).

EXAMPLE 2

Determination of the Keratinocyte Proliferation

The keratinocytes used were obtained from a skin specimen originating from plastic surgery. They are used at second passage.

The keratinocytes are cultured at 37° C. in a humid atmosphere (5% $CO_2$) according to the method of Rheinwald and Green, in the presence of 3T3 fibroblasts treated with mitocyne, in MEM medium containing 10% foetal calf serum (FCS), 0.4 μg/ml of hydrocortisone, 10 ng/ml of EGF and $10^{-9}$ M cholera toxin. The 3T3 cells are seeded 24 hours before the keratinocytes in a proportion of 15,000 cells per $cm^2$ in 10 $cm^2$ cluster wells. Then, the keratinocytes are seeded in a proportion of 4000 cells per $cm^2$.

The cells are treated for 4 hours, per keratinocyte seeding, with the products diluted in DMSO. The final concentration of DMSO in the culture medium does not exceed 0.2% (v/v). After three days of culture, the solution of 5-bromo-2'-deoxyuridine (BrdU, cell proliferation kit from Boehringer ref 1 674629) diluted to 1/100 is added to the culture medium.

After denaturation of the DNA, the anti-BrdU-POD (peroxidase) antibody is added according to the manufacturer's indications. After 1 hour of incubation, the substrate solution is added and reading of the optical density is carried out at 370 nM in an ELISA reader.

Thus, the compounds A and E described in Example 1 show a % of inhibition of keratinocyte proliferation which is less than or equal to 20% when they are used at a concentration which is lower than or equal to 100 nM.

EXAMPLE 3

Materials and Methods

Cell Culture Conditions

Normal human keratinocytes (NHK) were isolated from human skin obtained after plastic surgery and cultured by the method of Rheinwald and Green (Rheinwald J. G. and Green, H. Serial cultivation of strains of human epidermal keratinocytes: the formation of keratinizing colonies from single cells. Cell, 1975, 6, 331–343). The cells were cultured in a complete medium (MCDB 153) containing 0.5 mM $CaCl_2$. MCDB 153 complete medium is composed of a basal medium (KBM, Clonetics, San Diego, Calif.) to which 0.4% (v/v) bovine pituitary extract, 5 μg/ml of insulin and 10 ng/ml of epidermal growth factor (EGF) have been added.

When the cells have reached about 60% confluence (day 0), the medium is replaced with an MCDB 153 complete medium containing either 0.15 mM $CaCl_2$ (low calcium medium) or 1.15 mM $CaCl_2$ (high calcium medium). The medium is changed every two days.

Epidermis Reconstructed on a Dermal Equivalent of Type 1 Collagen

Adult interfollicular epidermis cells, which were isolated from the skin of human breast obtained after plastic surgery, were amplified (Rheinwald J. G. and Green, H. Serial cultivation of strains of human epidermal keratinocytes: the formation of keratinizing colonies from single cells. Cell, 1975, 6, 331–343) and stored in liquid nitrogen. The cells were thawed and seeded on a dermis equivalent of type I collagen (Asselineau, D., Bernard, B. D. and Darmon, M. Three-dimensional culture of human keratinocytes on a dermal equivalent. A model to study epidermal morphogenesis and differentiation in vitro. In: Maibach, H., Lowe, N. (eds.) Models in Dermatology. Karger, Basle, 1987, 1987, 1–7). The cultures were first of all immersed in the culture medium for one week to obtain a confluent monolayer (day 0), and were then put at the air-liquid interface to produce a stratified and keratinized epithelium. The culture medium consisted of a minimum essential medium (MEM) to which 10% (v/v) foetal calf serum, EGF (10 ng/ml), hydrocortisone (0.4 µg/ml) and a cholera toxin (10–9 M) were added. The medium was changed three times a week.

The morphology of the reconstructed skin was evaluated by staining vertical paraffin sections with hemalum-phloxin-saffron.

Biopsies

Biopsies were obtained from involved and uninvolved psoriatic skin after agreement of the patients. The biopsies were immediately immersed in an RNA extraction solution (4 M guanidium thiocyanate). It were then frozen in liquid nitrogen and kept at −80° C. until their use.

Isolation of RNAs

All the RNAs originating from the keratinocytes in culture or from reconstructed skin were isolated using the Trizol (Gibco BRL) method, according the manufacturer's procedure, and conserved at −80° C. until their use. All the RNAs originating from the skin biopsies were prepared as described by Chomczynski and Saachi (Chromczynski, P. and Saachi, N. Single-step method of RNA isolation by acid guanidium thiocyanate-phenol-chloroform extraction. Anal. Biochem., 1987, 162, 156–159).

RT-PCR and Semi-quantitative PCR

The PCR oligonucleotides- were synthesized by Gibco BRL (France), and have the sequence described below:
GAPDH sense oligonucleotide (5'-AATCCCATCACCATCTTCCA-3') and antisense oligonucleotide (5'-GTCATCATATTTGGCAGGTT-3'); sense oligonucleotide for PPARα (5'-TCATCAAGAAGACGGAGTCG-3') and antisense oligonucleotide (5'-CGGTTACCTACAGCTCAGAC-3'); sense oligonucleotide for PPARγ (5'-ATGACAGCGAACTTGGCAATA-3') and antisense oligonucleotide (5-CGAACTGGAAGAAGGGAAAT-3'); sense oligonucleotide for keratin 1 (5-AGTTCCAGCGTGAGGTTTGT-3') and antisense oligonucleotide (5'-GGGACTGAGATTGCCACTGA-3); sense oligonucleotide for loricrin (5'-ACCACGGAGGCCGAAGGAGTT-3') antisense oligonucleotide (5'-CTGGGGTTGGGAGGAGGTAGTTG-3'); sense oligonucleotide for transglutaminase type I (TGI) (5'-GCGGCAGGAGTATGTTCTTA-3') and antisense oligonucleotide (5'-AGGGATGTGTCTGTGTCGTG-3'). The amplified products are equal to 558 bp for GAPDH; 211, 287 and 341 bp for PPARα, δ and γ, respectively; 250 bp for keratin 1; 189 bp for loricrin and 444 bp for TGI.

The RT-PCR was carried out using 5 µg of the RNAs which were extracted from the cultured cells, from the reconstructed skins or from the skin biopsies. After denaturation in diethyl-pyrocarbonate-treated water for 10 minutes at 70° C., the RNAS were reverse-transcribed into cDNA using the "SuperScript II RNase H- reverse trascriptase kit (10 units/reaction, Gibco BRL) and 0.5 µg of oligo (dT) as primer, at 42° C. for 50 min, for a total buffer volume of 20 µl (20 mM Tris-HCl, pH 8.4–50 mM KCL, 1.5 m=mM MgCl2, 1 mM dNTP, 10 mM DTT, and 20 units of RNase inhibitor). The mixture was inactivated at 70° C. for 15 min and treated with RNaseH at 37° C. for 20 min. In each case, samples containing no reverse transcriptase (negative control) were included. The PCR amplification was carried out with a PTC 225 machine (MJ Research), after a one minute period of denaturation at 94° C., under the following conditions: denaturation at 94° C. for 30 seconds, annealing at 55° C. for 30 seconds and extension at 72° C. for 30 seconds, over a total of 30 cycles.

The reaction mixture contains 20 mM Tris-HCl, pH 8.4, 50 mM KCl, 1.5 mM $MgCl_2$, 0.1 µM oligonucleotide primers, 100 µM dNTP, 0.5 units of Taq DNA polymerase P and 5 µl of the cDNA mixture diluted to 1/100. The final product was heated for 3 minutes at 72° C.. In each case, positive controls for RT (containing cDNA encoding the PPARs) and a PCR negative control (without DNA) were included. The PCR products were separated by electrophoresis on 2% agarose gels containing 1 µg/ml of ethidium bromide, photographed, and their identity was confirmed by Southern blot.

The semi-quantitative PCR was carried out as described above, except that the concentrations of dNTP were 100 µM dATP, dGTP, dTTP, 10 µM dCTP, 0.5 µCi of [32P] dCTP. The PCR products were then separated using 6% (weight/v) acrylamide gels. The radioactivity of each band was quantified by the phosphorimaging technique. The screens were scanned using a FUJI BAS 2000, and the signal was quantified in PSL (Photo Stimulating Luminescence) units using an image analysis program (Tina). The results were analysed for each sample, comparing the intensity of the band with that of GAPDH. An optimum number of PCR cycles was determined in the linear amplification region. 10-fold serial dilutions of the cDNA mixture were made to control the linear correlation between the intensity of the radioactive signal and the initial quantity of DNA.

Results

The first experiments, using Northern-blot analysis of total RNA originating from NHK in culture, showed that PPARδ is present in almost equal amounts in undifferentiated and differentiated keratinocytes, whereas the PPARα and -γ were not detected.

To analyse the expression of the PPARs, RT-PCR analysis was carried out using oligonucleotides which are specific for PPAR subtypes. The PCR products of 211 bp, 287 bp and 341 bp, corresponding respectively to the PPARα, -δ and -γ, were obtained after electrophoresis. The specificity of the PCR products was verified using plasmids containing CDNAs which encode the PPARs. In addition, Southern-blot analysis was carried out to identify the PCR products. The three PPAR subtypes were detected both in the undifferentiated NHKs which were obtained at 60% confluence in a low calcium medium, and in the differentiated NHKs which were obtained after 4 days of culture in a high calcium medium.

Next, semi-quantitative PCR analysis was carried out to compare the level of expression of the PPAR subtypes in the NHKs which were cultured in a low calcium medium or in a high calcium medium. The expression of the PPARα gene increases slowly from day 0 to day 4 in a low calcium medium (1.7 times) and in a high calcium medium (2.6 times). After 4 days, the expression of the PPARδ gene increased both in the low calcium and in the high calcium media (4.5 and 5.8 times, respectively). The level of expression of the PPARγ gene remains unchanged for 4 days in a low calcium medium, whereas it increases surprisingly between the $3^{rd}$ and the $4^{th}$ day after the cells have been cultured in a high calcium medium (4.5 times).

Since the keratinocyte differentiation is incomplete under immersed culture conditions, we used reconstructed skin in vitro, which shows a more complete stratification and keratinization of the epidermis, to study the expression of PPARs. 2 days after the emersion, only two or three layers of keratinocytes are present; 2 days later, the keratinocytes are organized in a thin multilayer epithelium, whereas after 7 days, the epidermis is composed of an epithelium which resembles normal human epidermis. Studies by immunofluorescence have shown that differentiation markers, such as involucrin, filagrin and TGI (transglutaminase I), are expressed and located as described in Asselineau, D., Bernard, B. D. and Darmon, M. Three-dimensional culture of human keratinocytes on a dermal equivalent. A model to study epidermal morphogenesis and differentiation in vitro. In: Maibach, H., Lowe, N. (eds.) Models in Dermatology. Karger, Basle, 1987, 1–7.

The level of expression of the three PPAR subtypes during the reconstruction of the epidermis is as follows:

The PPARα RNA is slightly increased (2 times) after 7 days of emersion. The level of PPARδ remains constant from day 0 to day 7. Conversely, the expression of PPARγ increases by 7 times between day 0 and day 7.

The mode of expression of the PPAR subtypes during the reconstruction of the skin was compared to that of the keratinocyte differentiation markers. The maximum expression of keratin 1, of loricrin and of TGI was observed 7 days after the emersion.

To analyse the expression of the PPAR subtypes in human skin, total RNAs were prepared from non-lesioned or lesioned psoriatic epidermis and subjected to RT-PCR semi-quantitative analysis. The expression of PPARα is only slightly decreased in lesioned skin, whereas the expression of PPARγ is considerably decreased (about 3.5 times). However, the expression of PPARδ increases in lesioned epidermis with respect to non-lesioned epidermis.

DISCUSSION

The three PPAR subtypes have been described in amphibians, rodents and humans. (Issemann, I. and Green, S. Activation of a member of the steroid hormone receptor superfamily by peroxisome proliferators. 1990, Nature, 347, 647–650—Sher, T., Yi, H.-F., McBride, O. W. and Gonsalez, F. J. cDNA cloning, chromosomal mapping, and functional characterization of the human peroxisome proliferator activated receptor. Biochemistry, 1993, 32, 5598–5604—Zhu, Y., Alvares, K., Huang, Q., Rao, H. S. and Reddy, J. K. Cloning of a new member of the peroxisome proliferator-activated receptor gene family from mouse liver. J. Biol. Chem., 1993, 268, 26817–26820—Greene, M. E., Blumberg, B. McBride, O. W., Yi, H. F., Kronquist, K., Kwan, K., Hsieh, L., Greene, G. and Nimer, S. D. Isolation of the human peroxisome proliferator activated receptor gamma cDNA: expression in hematopoietic cells and chromosomal mapping. Gene Expression, 1995, 4, 281–299—Elbrecht, A., Chen, Y., Cullinan, C. A., Hayes, N., Leibowitz, M. D., Moller, D. E. and Berger, J. Molecular cloning, expression and characterization of human 1 and γ2. Biochem. Biophys. Res. Comm., 1996, 224, 431–437—Lambe, K. G. and Tugwood, J. D. A human peroxisome-proliferator-activated receptor-γ is activated by inducers of adipogenesis, including thiasolidinedione drugs, Eur. J. Biochem., 1996, 239, 1–7—Schmidt, A., Endo, N., Rutledge, S. J., Vogel, R., Shinar, D. and Rodan, G. A. Identification of a new member of a steroid hormone receptor superfamily that is activated by a peroxisome proliferator and fatty acids. Mol. Endocrinol., 1992, 6, 1634–1641—Kliewer, S. A., Forman, B. M., Blumberg, B., Ong, E. S., Borgmeyer, U., Mangelsdorf, D. J., Umesoto, K. and Evans, R. M. Differential expression and activation of a family of murine peroxisome proliferator-activated receptor. Proc. Natl. Acad. Sci. USA, 1994, 91, 7355–7359—Amri, E.-Z, Bonino F., Ailhaud, G., Abumrad, N. A. and Grimaldi, P. A. Cloning of a protein that mediated transcriptional effects of fatty acids in preadipocytes. J. Biol. Chem., 1995, 270, 2367–2371—Dreyer, C., Krey, G., Keller, H., Givel, F., Helftenbein, G. and Wahli, W. Control of the peroxisomal beta-oxidation pathway by a novel family of nuclear hormone receptors. Cell, 1992, 68, 879–887). PPARα is strongly expressed in tissues which show a high level of fatty acid oxidation and of peroxisomal metabolism, such as the liver, the heart, the kidney and the intestine. PPARδ is expressed abundantly and in an omnipresent manner, whereas the expression of PPARγ is predominantly in tissues with active lipogenesis, such as white adipose tissue, but it is also found in the cells of the immune system (Issemann, I. and Green, S. Activation of a member of the steroid hormone receptor superfamily by peroxisome proliferators. 1990, Nature, 347, 647–650—Kliewer, S. A., Forman, B. M., Blumberg, B., Ong, E. S., Borgmeyer, U., Mangelsdorf, D. J., Umesoto, K. and Evans, R. M. Differential expression and activation of a family of murine peroxisome proliferator-activated receptor. Proc. Natl. Sci. USA, 1994, 91, 7355–7359—Lehmann, J. M., Moore, L. B., Smih-Oliver, T. A., Wilkinson, W. O., Wilson, T. M. and Kliewer, S. A. An antidiabetic thiasolidinedione is a high affinity ligand for peroxisome proliferator activated receptors γ (PPARγ) J. Biol. Chem., 1995, 270, 12953–12956—Braissant, O., Foufelle, F., Scotto, C., Dauca, M. and Wahli, W. Differential expression of proxisome proliferator-activated receptor (PPARs): tissue distribution of PPAR-α, -β and -γ in the adult rat, Endocrinology, 1996, 137, 354–366—Tontonoz, P., Hu, E., Graves, R. A., Budavari, A. I. and Spiegelman, B. M. mPPARγ2n tissue-specific regulator of an adipocyte enhancer. Genes Dev., 1994, 8, 1224–1234). The tissue specific distribution of the three PPAR subtypes might explain their different physiological action. PPARα and PPARγ appear to regulate the two branches of lipid homeostasis, i.e. respectively fatty acid catabolism and lipogenesis. Whereas the omnipresent expression of PPARδ suggests a biological function which is general, but which is still unknown.

The process of differentiation of the keratinocytes of the epidermis is accompanied by an accumulation of specific lipids which are responsible for the formation of the barrier function of the epidermis. However, little is known about the level of expression or the role of the PPAR subtypes in the epidermis. A recent study has shown that the constitutive expression of a dominant-negative mutant of RARα in the suprabasal cells of the epidermis of mice results in a decreased barrier function of the skin (Imakado, S., Bickenbach, J. R., Bundman, D. S., Rothnagel, J. A., Attar, P. S., Wany, X.-J., Walczak, V. R., Wisniewski, S., Pote, J., Gordon, J. S., Heyman, R. A., Evans, R. M. and Roop, D. R. Targeting expression of a dominant-negative retinoic acid receptor mutant in the epidermis of transgenic mice results in loss of barrier function. Genes Dev., 1995, 9, 317–329). It has been suggested that the mutated RARα is capable of sequestering RXR, which is required for the formation of the PPAR-RXR heterodimer (Keller, H., Dreyer, C., Medin, J., Mahfoudi, A., Ozato, K. and Wahli, W. Fatty acids and retinoids control lipid metabolism through activation of peroxisome proliferator-activated receptor—retinoid X receptor heterodimers. Proc. Natl. Acad. Sci. USA, 1993; 90; 2160–2164—Issemann, I., Prince, R. A. Tugwood, J. D. and Green, S. The retinoid X receptor enhances the function of the peroxisome proliferator activated receptor. Biochimie, 1993, 75, 251–256). This implies that the inactivation of PPARα is partly responsible for the loss of the barrier function of the epidermis in the transgenic mice.

Thus, we demonstrate herein that the three PPAR subtypes are expressed in human keratinocytes. PPARδ shows the highest level of expression, whereas PPARα and PPARγ are expressed at a low level. The absence of expression of the PPAR gene, which has been reported in interfollicular keratinocytes of rats (Braissant, O., Foufelle, F., Scotto, C., Dauca, M. and Wahli, W. Differential expression of proxisome proliferator-activated receptor (PPARs): tissue distribution of PPAR-α, -β and -γ in the adult rat, Endocrinology, 1996, 137, 354–366), may be due to the insufficient sensitivity of the hybridization technique and/or of the difference in the species studied.

Our results clearly show that the expression of PPARγ, and to a certain extent, that of PPARα, is related to the differentiation of keratinocytes. The expression of PPARγ in NHKs which are cultured for four days in a high calcium medium increases noticeably.

This observation was confirmed using a model of reconstructed skin, in which the expression of PPARγ increases during stratification and keratinization of the epidermis. The expression of PPAR was compared to the increase in the various markers (keratin 1, TGI and loricin), which are normally expressed in the suprabasal compartment of normal epidermis. This strongly suggests that the expression of PPAR-γ takes place in the suprabasal layers of the human epidermis and is related to the differentiation of NHKs.

The expression of the PPAR subtypes was also determined in lesioned and non-lesioned psoriatic epidermides. A decrease in the levels of PPARα and of PPARγ was observed in hyperproliferating lesioned epidermis, which shows once again that the expression of the two subtypes is dependent on the differentiation state of the epidermis. The expression of PPARδ increases in lesioned epidermides, which leads to the suggestion that the expression of this subtype might be associated with keratinocyte proliferation.

In conclusion, we have demonstrated that using cultures which are submerged or exposed to the air, that the expression of the PPARα and -γ genes increase during keratinocyte differentiation, whereas the expression of PPARδ is not modified. In hyperproliferative psoriatic epidermis, the expression of PPAR-γ decreases, which shows that this subtype is related to keratinocyte differentiation.

What is claimed is:

1. A method for treating skin disorders related to an abnormality of the differentiation of epidermal cells comprising administering an effective amount of at least one activator of receptors of the PPAR-γ type wherein the disorder related to an abnormality of the differentiation of epidermal cells is selected from the group consisting of psoriasis, eczema, lichen planus, skin lesions associated with lupus, dermatitides, seborrho or solar dermatitis, keratoses, senile, actinic, light-induced or follicular keratosis, common acne, keloids, nevi, warts, and ichthyoses and wherein the activator of receptors of the PPAR-γ type is selected from the group consisting of 5-{4-[2-(methyl-pyrid-2-ylamino)ethoxy]benzl}thiazolidine-2,4-dione; 3-{4-[2-(benzoxazol-2-ylmethylamino)ethoxy]phenyl}-2-ethoxypropionic acid; (+)-3-{4-[2-(benzoxazol-2-ylmethylamino)ethoxy]phenyl}-2-ethoxypropionic acid; and (−)-3-{4-[2-(benzoxazol-2-ylmethylamino)ethoxy]phenyl}-2-ethoxypropionic acid.

2. The method according to claim 1, wherein the activator of receptors of the PPAR-γ type has an AC50 relative to PPAR-γ which is lower than or equal to 200 nM.

3. The method according to claim 2, wherein the activator of receptors of the PPAR-γ type is specific.

4. The method according to claim 3, wherein the activator of receptors of the PPAR-γ type has a ratio R1 of AC50 relative to PPAR-γ over AC50 relative to PPARα which is lower than or equal to 0.05.

5. The method according to claim 1, wherein the activator of receptors of the PPAR-γ type used has a percentage of inhibition of keratinocyte proliferation which is less than or equal to 20% when it is used at a concentration which is lower than or equal to 100 nM.

6. The method according to claim 1, wherein the pharmaceutical composition is packaged in a form for application via the topical route.

7. The method according to claim 6, wherein the activator of receptors of the PPAR-γ type is used at a concentration generally between 0.001% and 10% by weight, relative to the total weight of the composition.

8. The method according to claim 2, wherein the activator of receptors of the PPAR-γ type have an AC50 relative to PPAR-γ which is lower than or equal to 50 nM.

9. The method according to claim 7, wherein the activator of receptors of the PPAR-γ type is used at a concentration generally between 0.01% and 10% by weight.

* * * * *